United States Patent [19]
Asato et al.

[11] Patent Number: 4,886,829
[45] Date of Patent: Dec. 12, 1989

[54] 23-OXO (KETO) AND 23-IMINO DERIVATIVES OF MONO- AND DIEPOXY LL-F28249 COMPOUNDS

[75] Inventors: Goro Asato, Titusville; Susan Y. Tamura, Hamilton Square, both of N.J.

[73] Assignee: American Cyanamid Company, Stamford, Conn.

[21] Appl. No.: 22,850

[22] Filed: Mar. 6, 1987

[51] Int. Cl.$^4$ .................. A61K 31/335; C07D 313/96
[52] U.S. Cl. ..................................... 514/450; 549/264
[58] Field of Search ......................... 549/264; 514/450

[56] References Cited

U.S. PATENT DOCUMENTS

| | | | |
|---|---|---|---|
| 4,201,861 | 5/1980 | Mrozik et al. | 536/7.1 |
| 4,289,760 | 9/1981 | Mrozik et al. | 536/7.1 |
| 4,423,209 | 12/1983 | Mrozik | 549/264 |
| 4,530,921 | 7/1985 | Mrozik | 549/264 |
| 4,547,520 | 10/1985 | Ide et al. | 549/264 |
| 4,579,864 | 4/1986 | Linn et al. | 549/264 |
| 4,696,922 | 9/1987 | Sturm et al. | 549/264 |

FOREIGN PATENT DOCUMENTS

| | | |
|---|---|---|
| 170006 | 2/1986 | European Pat. Off. . |
| 2166436 | 5/1986 | United Kingdom . |
| 2176182 | 12/1986 | United Kingdom ................ 549/264 |

*Primary Examiner*—Glennon H. Hollrah
*Assistant Examiner*—Ba Trinh
*Attorney, Agent, or Firm*—Estelle J. Tsevdos

[57] ABSTRACT

The present invention relates to novel 23-oxo (keto) and 23-imino derivatives of certain C(26,27)-epoxy- and C(14,15;26,27)-diepoxy-LL-F28249 compounds. The LL-F28249 compounds (collectively) are isolates from the fermentation broth of *Streptomyces cyaneogriseus* subspecies *noncyanogenus* having deposit accession no. NRRL-15773. The derivatives are obtained by oxidation of the 23-hydroxy group of 5-O-silylated-C(26,27)-epoxy and C(14,15;26,27)diepoxy-LL-F28249 compounds, followed by desilylation and derivatization with amino compounds. The novel compounds have anthelmintic, ectoparasiticidal, nematicidal, insecticidal and acaricidal activity and are, therefore, useful in the treatment of infections in warm-blooded animals and infestations in agricultural crops. Compositions containing the present compounds as active ingredients thereof also are presented.

22 Claims, No Drawings

23-OXO (KETO) AND 23-IMINO DERIVATIVES OF MONO- AND DIEPOXY LL-F28249 COMPOUNDS

BACKGROUND OF THE INVENTION

The present invention relates to new 23-oxo (keto) and 23-imino derivatives of the compounds C(26,27)-epoxy and C(14,15;26,27)-diepoxy-LL-F28249 compounds collectively defined as LL-F28249. These LL-F28249 compounds are produced by the fermentation of the microorganism *Streptomyces cyaneogriseus* subspecies noncyanogenus having deposit accession no. NRRL-15773. The morphological characteristics, compounds and methods for their production are disclosed in European Application No. 170,006, incorporated herein by reference. The C(26,27)-epoxy- and C(14,15;26,27)-diepoxy-LL-F28249 compounds are derived by epoxidation of the LL-F28249 compounds and disclosed in concurrently filed U.S. application for Letters Pat. Ser. No. 022847, Asato et al, hereby incorporated by reference.

The C(26,27)-epoxy- and C(14,15;26,27)-diepoxy-LL-F28249α, β, ε, ζ, θ and ι compounds are complex macrolids which have a 23-hydroxy substituent, as well as hydroxy groups at the 5 and 7 positions. The selective oxidation of the 23-hydroxy group to a 23-oxo (keto) group and the subsequent derivatization of the oxo group to afford 23-imino derivatives are the subject matter of the present invention. These 23-oxo (keto) and 23-imino derivatives of the C(26,27)-epoxy and C(14,15;26,27)-diepoxy-LL-F28249α, β, ε, ζ, θ and ι compounds are useful for the prevention, treatment or control of helminths, ectoparasites, insects, acarids and nematodes in warm-blooded animals and agricultural crops.

SUMMARY OF THE INVENTION

The present invention provides novel 23-oxo (keto) and 23-imino derivatives of C(26,27)-epoxy- and C(14,15;26,27)-diepoxy-LL-F28249α, β, ε, ζ, θ and ι.

The LL-F28249 compounds have the following structural formula:

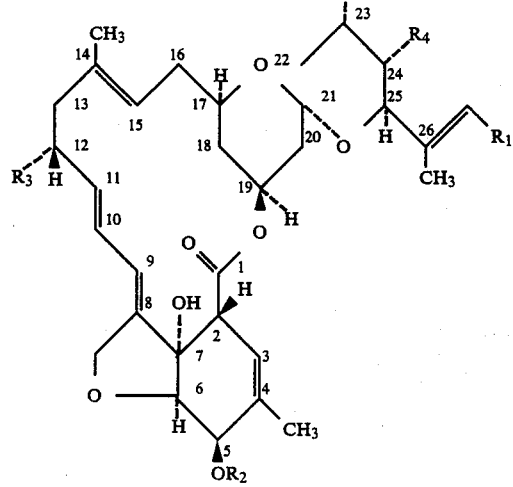

| Component | $R_1$ | $R_2$ | $R_3$ | $R_4$ |
|---|---|---|---|---|
| LL-F28249α | $CH(CH_3)_2$ | H | $CH_3$ | $CH_3$ |
| LL-F28249β | $CH_3$ | H | $CH_3$ | $CH_3$ |

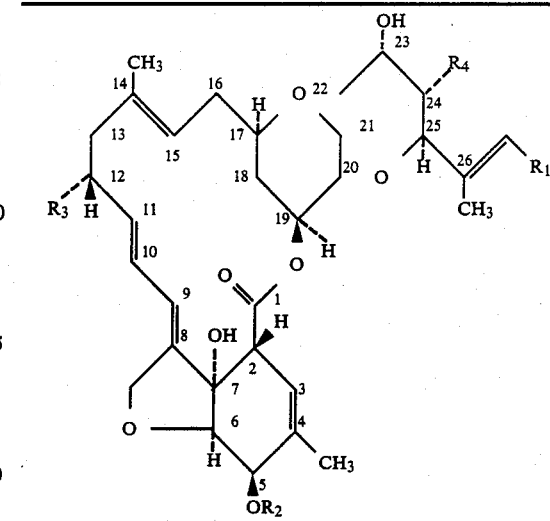

| Component | $R_1$ | $R_2$ | $R_3$ | $R_4$ |
|---|---|---|---|---|
| LL-F28249ε | $CH(CH_3)_2$ | H | H | $CH_3$ |
| LL-F28249ζ | $CH_2CH_3$ | H | $CH_3$ | $CH_3$ |
| LL-F28249θ | $CH(CH_3)_2$ | H | $CH_3$ | $CH_2CH_3$ |
| LL-F28249ι | $CH(CH_3)_2$ | H | $CH_2CH_3$ | $CH_3$ |

The C(26,27)-epoxy- and C(14,15;26,27)-diepoxy-LL-F28249α, β, ε, ζ and ι have the following structure,

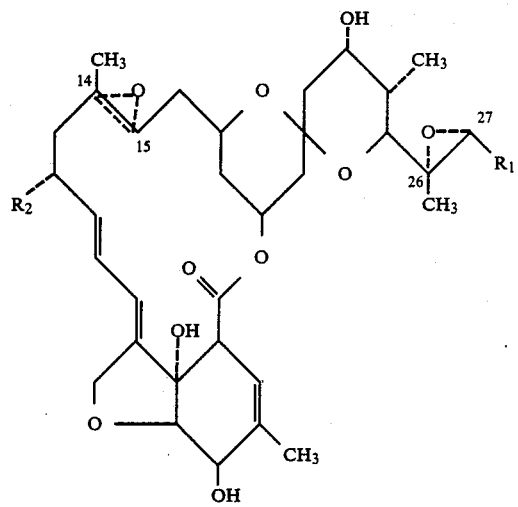

wherein $R_1$ is methyl or isopropyl; $R_2$ is hydrogen, methyl or ethyl; and the dotted triangular figure with oxygen at C(14,15) indicates that either a double bond or an epoxide is present.

The compounds of the present invention are useful anthelmintics, ectoparasiticides, insecticides, acaricides and nematicides in treating, preventing or controlling such diseases in warm-blooded animals, such as poultry, cattle, sheep, swine, rabbits, horses, dogs, cats and human beings and agricultural crops.

Although these diseases have been recognized for years and therapies exist for the treatment and prevention of the diseases, the present invention provides therapeutically or pharmaceutically effective amounts of the present novel compounds. For instance, U.S. application for Letters Pat. Ser. Nos. 907,283, 907,188, 907,281, 907,259, 907,187 and 907,284 of Asato and Asato et al., filed on September 12, 1986 and incorporated herein by references thereof provide compounds for such treatments. Also U.S. application for Letters Pat. Ser. Nos. 022849, 022906, 022848, 022846 and 022847, of Asato et al. filed concurrently herewith and incorporated herein by reference thereof provide compounds for such treatments.

U.S. Pat. No. 3,950,360, Aoki et al, April 13, 1976 discloses certain antibiotic substances obtained by culturing a Streptomyces microorganism, said compounds being useful as insecticides and acaricides. Further, an entire series of U.S. patents relates to certain compounds produced by the fermentation of Streptomyces avermitilis (U.S. Pat. No. 4,171,314, Chabala et al., October 16, 1979; U.S. Pat. No. 4,199,569, Chabala et al., April 22, 1980; U.S. Pat. No. 4,206,205, Mrozik et al., June 3, 1980; U.S. Pat. No. 4,310,519, Albers-Schonberg, January 12, 1982; U.S. Pat. No. 4,333,925, Buhs et al, June 8, 1982). U.S. Pat. No. 4,423,209, Mrozik, December 27, 1983 relates to the process of converting some of these less desirable components to more preferred ones. Finally, British Patent Application No. 2166436 A discloses antibiotics also, as does Belgium Patent Application No. 904,709A.

The present compounds or the pharmaceutically and pharmacologically acceptable salts thereof exhibit excellent and effective treatment, prevention and/or control of these serious diseases of warm-blooded animals.

It is an object of the present invention, therefore, to provide novel C(26,27)-epoxide and C(14,15; 26,27)-diepoxide derivatives of LL-F28249α, β, ε, ζ, θ and ι. It is a further object to provide a process for the preparation of these derivatives and to provide methods for preventing, treating or controlling endo- and ectoparasitic (collectively parasitic) insect, nematode and acarid infections and infestations in warm-blooded animals and agricultural crops by providing compositions containing prophylactically, therapeutically, pharmaceutically or pesticidally effective amounts of the present compound. A further object of these compounds is as intermediates for the preparation of other novel antiparasitic and insecticidal compounds.

These and other objects of the invention will become apparent by the more detailed description of the invention provided hereinbelow.

DETAILED DESCRIPTION OF THE INVENTION

The LL-F28249 compounds have the following structural formula,

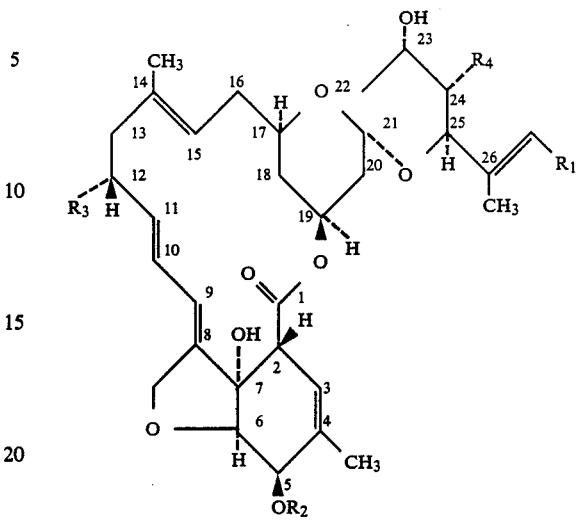

| Component | $R_1$ | $R_2$ | $R_3$ | $R_4$ |
|---|---|---|---|---|
| LL-F28249α | $CH(CH_3)_2$ | H | $CH_3$ | $CH_3$ |
| LL-F28249β | $CH_3$ | H | $CH_3$ | $CH_3$ |
| LL-F28249ε | $CH(CH_3)_2$ | H | H | $CH_3$ |
| LL-F28249ζ | $CH_2CH_3$ | H | $CH_3$ | $CH_3$ |
| LL-F28249θ | $CH(CH_3)_2$ | H | $CH_3$ | $CH_2CH_3$ |
| LL-F28249ι | $CH(CH_3)_2$ | H | $CH_2CH_3$ | $CH_3$ |

The C(26,27)-epoxy- and C(14,15;26,27)-diepoxy-LL-F28249α, β, ε, ζ, θ and ι have the following structure,

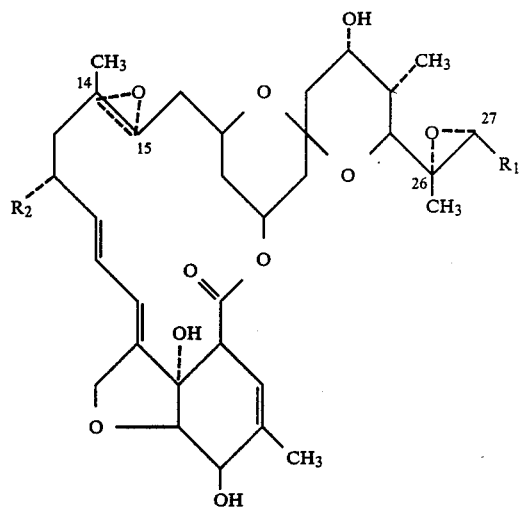

wherein $R_1$ is methyl or isopropyl; $R_2$ is hydrogen, methyl or ethyl; and the dotted triangular figure with oxygen at C(14,15) indicates that there is present either a double bond or an epoxide is present.

The compounds of the present invention are represented by the following structural formulae (I),

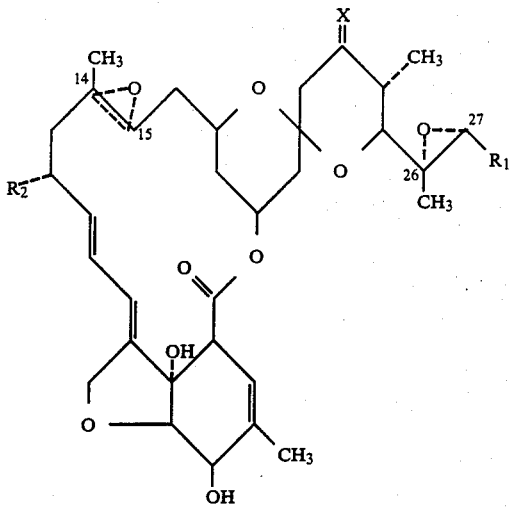

wherein $R_1$ is methyl or isopropyl; $R_2$ is hydrogen, methyl or hydrogen; X is oxygen, $NOR_3$, or $N-NHR_4$; $R_3$ is hydrogen, $C_1-C_6$ alkyl, benzyl, allyl, propargyl, phenyl, $CH_2COO$-alkyl ($C_1-C_4$), N-($C_1-C_6$ alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1-C_6$ alkanoyl, chloroacetyl, methoxyacetyl, phenylacetyl, benzoyl and chlorobenzoyl; $R_4$ is

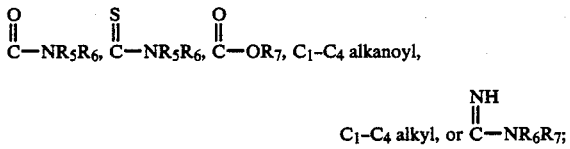

$R_5$ and $R_6$ are hydrogen or $C_1-C_4$ alkyl; and $R_7$ is $C_1-C_4$ alkyl; and the dotted triangular figure with oxygen at C(14,15) indicates that either a double bond or an epoxide is present.

Preferably, $R_1$ isopropyl; $R_2$ is methyl; X is oxygen, $NOR_3$ or $NNHR_4$; and $R_4$ is

$C_1-C_4$ alkanoyl or $C_1-C_4$ alkyl.

Another preferred compound is represented by $R_1$ being isopropyl; $R_2$ being methyl; X being oxygen, $NOR_3$ or $NNHR_4$; $R_4$ being

or $C_1-C_4$ alkanoyl; and the dotted triangular figure with oxygen at C(14,15) being a double bond.

The most preferred compound is represented by $R_1$ being isopropyl; $R_2$ being methyl; X being oxygen, $NOCH_3$,

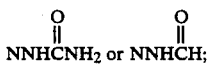

and the dotted triangular figure with oxygen at C(14,15) being a double bond.

The monoepoxide and diepoxide compounds which are precursors of the novel compounds of this invention are prepared by treating the appropriately protected LL-F28249 compound with a mild oxidizing agent at temperatures less than −15° C. The oxidant useful in the present invention is capable of selectively oxidizing the C(26,27) double bond as well as the C(14,15) double bond, but will leave other double bonds in the molecule intact. Selectivity also is attained by controlling the temperature of the oxidation in an inert solvent, such as methylene chloride, chloroform and the like. Peroxide oxidizing agents, such as m-chloroperoxybenzoic acid, are representative of the preferred oxidants in preparing the monoepoxy and diepoxy compounds of the present invention.

Generally, a slight excess of the oxidizing agent is employed such as 5%–20% excess, when it is desired to prepare the C(26,27) epoxide in good yield. When epoxidation at C(14,15) double bond also is desired equivalent to a slight excess of 2 moles is employed.

The epoxidation is generally conducted at temperatures less than −20° C. to −78° C. and is complete in 3–6 hours. Separation of the monoepoxide and the diepoxide is readily achieved by standard chromatographic techniques, such as column or preparative-plate chromatography.

The starting materials for the compounds of the present invention are the above-mentioned LL-F28249 fermentation products. These compounds are initially derivatized at the 5- and 23-hydroxy groups with a trisubstituted alkyl silyl group. A preferred protecting group is t-butyldimethylsilyl. The reaction is carried out by allowing the LL-F28249 compound to react with two molar equivalents of a substituted silyl halide, preferably a silyl chloride in an aprotic solvent such as dimethylformamide or ethylene dichloride in the presence of imidazole and/or 4-dimethylaminopyridine. The reaction is completed in 2–8 hours at 50° C. to 80° C.

The silyl group is removed after epoxidation by stirring the silyl derivative in methanol containing an acid, such as p-toluenesulfonic acid monohydrate or acetic acid. The reaction is complete in 1–8 hours at 0° C. to 25° C., preferably at 0° C. to 10° C. It also is especially beneficial if this reaction is conducted in the presence of a catalytic amount of $FeCl_3$.

In preparing the compounds of the present invention, the 5-hydroxy group is protected following the epoxidation. Therefore, prior to the oxidation of the 23-hydroxyl group to the 23-oxo or keto group, the 5-hydroxyl group is protected. Suitable protecting groups are trisubstituted silyl groups, such as t-butyldimethylsilyl and trimethylsilyl, or trisubstituted silyloxyacetyl groups, such as t-butyldimethylsilyloxy acetyl group. The protecting groups, however, are not limited to these groups since other useful protecting groups such as acyl and substituted acyl, such as acetyl, trifluoroacetyl, chloroacetyl, trichloroacetyl, phenoxyacetyl and the like, also are useful in the process of the present invention.

One of the preferred protecting groups is t-butyldimethylsilyl. This group is attached to the 5-hydroxyl group by reacting an unprotected 5-hydroxy C(26,27)-epoxy- or C(14,15;26,27)-diepoxy-LL-F-28249 compound with t-butyldimethylsilyl chloride in the presence of a base, such as imidazole, pyridine, 4-dimethylaminopyridine, triethylamine and the like, in an aprotic solvent such as methylene chloride, toluene, ethylacetate, tetrahydrofuran, ethylenedichloride and the like. The reaction is stirred at a temperature of about 0° C. to 30° C., and the reaction is complete in several hours, depending on the temperature of the reaction. The completion of the reaction is usually monitored by high performance liquid chromatography (HPLC) using reverse phase on a Whatman Partisil CCS/C$_8$ rapid analysis column.

Another preferred protecting group is t-butyldimethylsilyloxy acetyl group. This group is attached to the 5-hydroxyl group by combining the unprotected C(26,27)-epoxy- or C(14,15;26,27)-diepoxy-LL-F28249 compound in an aprotic solvent such as methylene chloride, toluene, ethyl acetate, tetrahydrofuran, ethylenedichloride and the like, containing a tertiary amine, such as pyridine or triethylamine, and adding the protecting agent in the form of an acid halide. The reaction is conducted at a temperature of about 0° C. to 30° C. and is monitored by HPLC for completion.

The 23-hydroxyl group of the protected C(26,27)-epoxy- or C(14,15;26,27)-diepoxy-LL-F28249 compound then is oxidized to the 23-oxo (or keto) group by using oxidizing agents such as pyridinium dichromate, pyridinium chlorochromate, chromic acid-dimethylpyrazole, acetic anhydride/dimethylsulfoxide, trifluoroacetic anhydride/dimethylsulfoxide, N-chlorosuccinimide/dimethylsulfoxide, oxalyl chloride/dimethylsulfoxide and the like. The reaction is carried out at dry-ice bath temperatures (about −78° C.) to room temperature (about 25° C.) and is complete in about 1 to 24 hours, depending on the rate of oxidation, which is monitored by HPLC. The dimethylsulfoxide oxidation procedures are carried out in the presence of triethylamine or diisopropylethylamine. Solvents such as methylene chloride, ethylenedichloride, dimethylformamide, dimethylsulfoxide and the like are used. In using oxalyl chloride/dimethylsulfoxide in the presence of triethylamine, it is advantageous to add molecular sieves to the reaction mixture to increase the yield. The oxidation may also be carried out by soil microorganisms using 100 mg to 10 g of a 23-hydroxy compound per liter of unsterilized soil at 20° C. to 30° C. The oxidized 23-keto compound is extracted from the soil by a solvent such as acetone, methanol or ethanol.

The silyl protecting group is removed by stirring a protected 23-keto-C(26,27)-epoxy or C(14,15;26,27)-diepoxy-LL-F28249 compound in a lower alkanol such as methanol at 0° C. to room temperature for about 0.5 hour to an hour in the presence of an acid such as p-toluenesulfonic acid. If the protecting group is a silyloxyacetyl group, the silyl group is removed with acid as described above, and the hydroxyacetyl group is cleaved with an equivalent of base such as sodium methoxide in methanol at 0° to room temperature in 0.5 hour to several hours. The silyloxyacetyl group may also be removed in one step by treatment with sodium methoxide at room temperature until the reaction is complete. Similarly, other acyl protecting groups are removed by base treatment.

The imino derivatives of the 23-oxo compounds are readily prepared by standard techniques such as procedures described by S. M. McElvain in *The Characterization of Organic Compounds*, published by MacMillan Company, New York, 1953, pages 204-205 and incorporated herein by reference.

Typically, a 23-oxo compound is stirred in alcohol, such as methanol or ethanol, or dioxane in the presence of acetic acid and an excess of the amino derivatizing agent, such as hydroxylamine hydrochloride, O-methylhydroxylamine hydrochloride, semicarbazide hydrochloride and the like along with an equivalent amount of sodium acetate, at room temperature to 50° C. The reaction is usually complete in several hours to several days at room temperature but can be readily speeded by heating.

The O-acyloximes or carbamoylated oximes are prepared by treating the oximes of structure (I) with acid anhydrides or isocyanates to afford (I), wherein $R_4$ is $C_1$-$C_6$ alkanoyl, chloroacetyl, methoxyacetyl, phenylacetyl, benzoyl, chlorobenzoyl, N-($C_1$-$C_4$ alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl or N-(benzyl)carbamoyl. The reactions are conducted in inert solvents, such as methylene chloride, ethylenedichloride or dioxane, in the presence of a tertiary amine, such as triethylamine or diisopropylethylamine. Generally, the reactions are conducted from 0° C. to room temperature, but if the reactions are sluggish, heat is applied. An equivalent to a slight excess of the acid anhydride is used to avoid reaction at the 5-hydroxy group.

The novel compounds of the present invention have significant activity as anthelmintics, ectoparasiticides, insecticides, nematicides and acaricides in human and animal health areas and in agriculture.

The disease or group of diseases described generally as helminthiasis is due to infection of an animal host with parasitic worms known as helminths. Helminthiasis is a prevalent and serious economic problem in domesticated animals such swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such Nematodirus, Cooperia, and Oesphagostomum primarily attack the intestinal tract while others, such as Haemonchus and Ostertagia, are most prevalent in the stomach. Still others such as Dictyocaulus are found in the lungs. Also, other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs, and if left untreated, may result in death of the infected host. The 23-oxo or -imino derivatives of the C(26,27)-epoxy or C(14,15;26,27)-diepoxy-LL-F28249 compounds of this invention unexpectedly have high activity against these parasites.

Additionally, they also are active against Dirofilaria in dogs, Nematospiroides, Syphacia, Aspiculuris in rodents, arthropod ectoparasites such as ticks, mites, lice, fleas, blowfly of animals and birds, the ectoparasite Lucilla sp. of sheep, biting insects and migrating dipterous larvae such as Hypoderma sp. in cattle, Gastrophilus in horses and Cuterebra sp. in rodents.

The compounds of the present invention also are useful in treating, preventing or controlling parasites which infect human beings, as well. The most common genera of parasites of the gastrointestinal tract of man are Ancylostoma, Necator, Ascaris, Strongyloides, Trichinella, Capillaria, Trichuris, and Enterobius. Other medically important genera of parasites which are found in the blood of other tissues and organs outside the gastrointestinal tract are the filiarial worms such as Wuchereria, Brugia, Onchocerca and Loa, Dracunculus and extra-intestinal stages of the intestinal worms Strongyloides and Trichinella. The present compounds also are of value against arthropods parasitizing man, biting insects and other dipterous pests causing annoyance to man.

These compounds further are active against household pests such as the cockroach, Blattella sp., clothes moth, Tineola sp., carpet beetle, Attagenus sp., and the housefly Musca domestica.

Insect pests of stored grains such as Tribolium sp., Tenebrio sp., and insect and acarid pests of agricultural plants such as spider mites (Tetranychus sp.), southern army worms, tobacco budworms, boll weevils, aphids (Acyrthiosiphon sp.), migratory orthopterans such as locusts and immature stages of insects living on plant tissue are controlled by the present compounds as well as the control of soil nematodes and plant parasites such as Meloidogyne sp., which may be of importance in agriculture.

The compounds of the present invention may be administered orally or parenterally for animal and human usage, while they may be formulated in liquid or solid form for agricultural use. Oral administration may take the form of a unit dosage form such as a capsule, bolus or tablet, or as a liquid drench where used as an anthelmintic for animals.

The animal drench is normally a solution, suspension or dispersion of the active compound, usually in water, together with a suspending agent such as bentonite and a wetting agent or like excipient. Generally, the drenches also contain an antifoaming agent. Drench formulations generally contain about 0.001% to 0.5%, by weight, of the active compound. Preferred drench formulations contain about 0.01% to 0.1% by weight.

Capsules and boluses comprise the active ingredient admixed with a carrier vehicle such as starch, talc, magnesium stearate or di-calcium phosphate.

Where it is desired to administer the 23-oxo or 23-imino derivatives of C(26,27)-epoxy or C(14,15;26,27)-diepoxy-LL-F28249 in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the active compound depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the active compounds of the present invention may be administered to animals parenterally, such as by intraruminal, intramuscular, intratracheal, or subcutaneous injection. In such an event, the active compound is dissolved or dispersed in a liquid carrier vehicle.

For parenteral administration, the active compound is suitably admixed with an acceptable vehicle, preferably of the vegetable oil variety such as peanut oil, cotton seed oil and the like. Other parenteral vehicles such as organic preparations using solketal, propylene glycol, glycerol formal, and aqueous parenteral formulation also are used. The active 23-oxo or -imino compound or compounds of the present invention are dissolved or suspended in the parenteral formulation for administration. Such formulations generally contain about 0.005% to 5%, by weight, of the active compound.

Although the compounds of the present invention are primarily used in the treatment, prevention or control of helminthiasis, they also are useful in the prevention and treatment of diseases caused by other parasites. For example, arthropod parasites such as ticks, lice, fleas, mites and other biting insects in domesticated animals and poultry are controlled by the present compounds. These compounds also are effective in treatment of parasitic diseases that occur in other animals including human beings. The optimum amount to be employed will, of course, depend upon the particular compound employed, the species of animal to be treated and the type of severity of parasitic infection or infestation. Generally, the amount useful in oral administration of these novel compounds is about 0.001 mg to 10 mg per kg of animal body weight, such total dose being given at one time or in divided doses over a relatively short period of time (1–5 days). The preferred compounds of the invention give excellent control of such parasites in animals by administering about 0.025 mg to 3 mg per kg of animal body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the animal's feed, or dissolved or suspended in the drinking water, compositions are provided in which the active compound or compounds are intimately dispersed in an inert carrier or diluent. An inert carrier is one that will not react with the active component and that will be administered safely to animals. Preferably, a carrier for feed administration is one that is, or may be, an ingredient of the animal ration.

Suitable compositions include feed premixes or supplements in which the active compound is present in relatively large amounts, wherein said feed premixes or supplements are suitable for direct feeding to the animal or for addition to the feed either directly or after an intermediate dilution or blending step.

Typical carriers or diluents suitable for such compositions include distillers' dried grains, corn meal, citrus meal, fermentation residues, ground oyster shells, wheat shorts, molasses solubles, corn cob meal, edible bean mill feed, soya grints, crushed limestone and the like. The active compounds are intimately dispersed throughout the carrier by methods such as grinding, stirring, milling or tumbling. Compositions containing about 0.005% to 2.0%, by weight, of the active compound are particularly suitable as feed premixes.

Feed supplements, which are fed directly to the animal, contain about 0.0002% to 0.3%, by weight, of the active compounds. Such supplements are added to the animal feed in an amount to give the finished feed the concentration of active compound desired for the treatment, prevention and/or control of parasitic diseases. Although the desired concentration of active compound will vary depending upon the factors previously mentioned as well as upon the particular derivative employed, the compounds of this invention are usually fed at concentrations of about 0.00001% to 0.02% in the feed in order to achieve the desired antiparasitic result.

The compounds also may be administered by pouring on the skin of animals via a solution. Generally, the active compounds are dissolved in a suitable inert solvent, such as dimethylsulfoxide, propylene glycol and the like, alternatively in combination of solvents, for the pour-on administration.

The compounds of this invention also are useful in combating agricultural pests that inflict damage upon growing or stored crops. The present compounds are applied, using known techniques such as sprays, dusts, emulsions and the like, to the growing or stored crops to effect protection from such agricultural pests.

The present invention is illustrated by the following examples which are illustrative of said invention and not limitative thereof.

EXAMPLE 1

5,23-O,O-(Bis-tert-butyldimethylsilyl)-LL-F28249α

In 20 mL of dimethylformamide, 2.0 g of LL-F28249α, 3.72 g of t-butyldimethylsilyl chloride and 2.38 g of imidazole are heated at 60° C. in an oil bath under $N_2$ for 6 hours. The mixture is cooled, quenched with 5 mL of $H_2O$ and diluted with 100 mL of $H_2O$ and 50 mL of brine. The product is then extracted from the aqueous mixture with $2 \times 50$ mL of $Et_2O$. The combined $Et_2O$ extracts are washed with $2 \times 25$ mL of $H_2O$, 10 mL of brine and dried over $MgSO_4$. Removal of $Et_2O$ affords the title compound that is identified by mass spectrometry and NMR spectroscopy.

EXAMPLES 2 and 3

LL-F28249α-C(26,27)-Epoxide and
LL-F28249α-C(14,15;26,27)-Diepoxide

In 5 mL of $CH_2Cl_2$, 105.4 mg of 5,23-O,O-(bis-t-butyldimethylsilyl)-LL-F28249α is dissolved and the solution is cooled in dry-ice/acetone bath, while 27.8 mg of m-chloroperoxybenzoic acid in 3 mL is slowly added dropwise. After an hour of stirring under $N_2$, the temperature is raised to $-42°$ C. for 2 hours and $-20°$ C. for an hour. The solution is washed with 1 mL of saturated $Na_2SO_3$ solution, 1 mL of saturated $NaHCO_3$ solution and 1 mL of brine. After drying over $Na_2SO_4$, the solution is evaporated, and the residue is chromatographed on silica gel in a flesh chromatography apparatus using 5% EtOAc/hexane followed by 10% EtOAc/hexane. Fractions 16 to 20 afford 45 mg of monoepoxide while fractions 31–36 afford 12.1 mg of diepoxide.

In 1 mL of MeOH, 30.3 mg of epoxide is stirred with 10.2 mg of p-toluenesulfonic acid monohydrate for 7.5 h under $N_2$. The mixture is diluted with 1 mL of saturated $NaHCO_3$ solution and 5 mL of $H_2O$ and extracted with $3 \times 2$ mL of $Et_2O$. The combined $Et_2O$ extracts are washed with brine, dried over $MgSO_4$, filtered and evaporated to dryness. The residue is chromatographed on silica gel using a flash chromatography apparatus and 2% isopropanol/$CH_2Cl_2$ as eluent to afford 9.4 mg of LL-F28249α-C(26,27)-epoxide, which is identified by mass spectrometry and NMR spectroscopy.

Similarly, the diepoxide is treated with p-toluenesulfonic acid to afford deblocked LL-F28249α-C(14,15;26,27)-diepoxide.

EXAMPLES 4-7

5,23-O,O-(Bis-tert-butyldimethylsilyl)-LL-F28249
compounds

Using the procedure of Example 1, the following bis-silylated products are prepared:

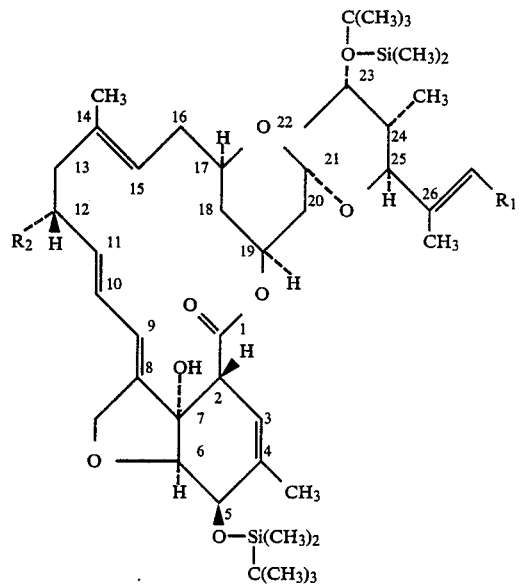

| $R_1$ | $R_2$ |
|---|---|
| $CH(CH_3)_2$ | H |
| $CH_2CH_3$ | $CH_3$ |
| $CH(CH_3)_2$ | $CH_2CH_3$ |
| $CH_3$ | $CH_3$ |

EXAMPLES 8-15

LL-F28249-C(26,27)-Epoxides and
LL-F28249-C(14,15;26,27)-Diepoxides

Using the method of Example 2, the following epoxides and diepoxides of structure (I) are prepared:

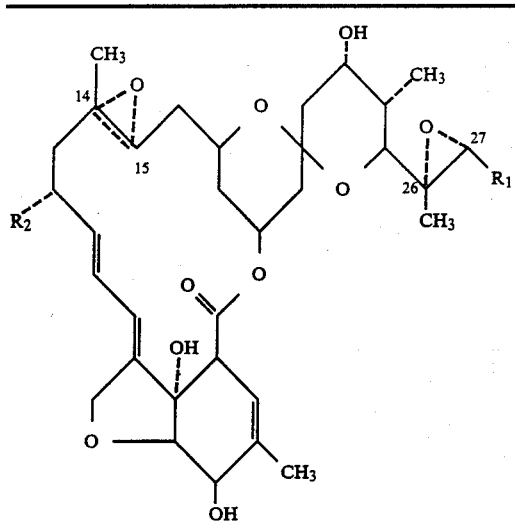

| R₁ | R₂ |
|---|---|
| CH(CH₃)₂ | H |
| CH₂CH₃ | CH₃ |
| CH(CH₃)₂ | CH₂CH₃ |
| CH₃ | CH₃ |

EXAMPLE 16

5-0-t-Butyldimethylsilyl-C(26,27)-epoxy-LL-F28249α

In 5 mL of CH₂Cl₂, 285 mg of C(26,27)-epoxy-LL-F28249α and 339 mg of imidazole are stirred in an ice bath and treated with 205 mg of t-butyldimethylsilyl chloride. The mixture is stirred at room temperature under N₂ atmosphere for 5 hours and diluted with an equal volume of ether. The mixture is then washed with H₂O and saturated NaCl solution, dried over MgSO₄ and evaporated to dryness. The glassy residue is purified by flash chromatography on silica gel using 1% isopropanol/heptane, followed by 2% isopropanol/heptane as eluent. Further purification by flash chromatography on silica gel using 100 mL of 10% EtOAc/heptane, followed by 100 mL of 20% EtOAc/heptane and evaporation of fractions from the latter elution affords the title compound, which is pure by high performance chromatography (HPLC), using 50% CH₃CN/50% H₂O in a curved gradient mode on a Whatman Partisil CCS/C₈ rapid analysis column at 1 mL/min. flowrate.

EXAMPLES 17-20

Using the method of Example 16, the following 5-0-t-butyldimethylsilyl-C(26,27)-epoxy-LL-F28249 compounds are prepared:

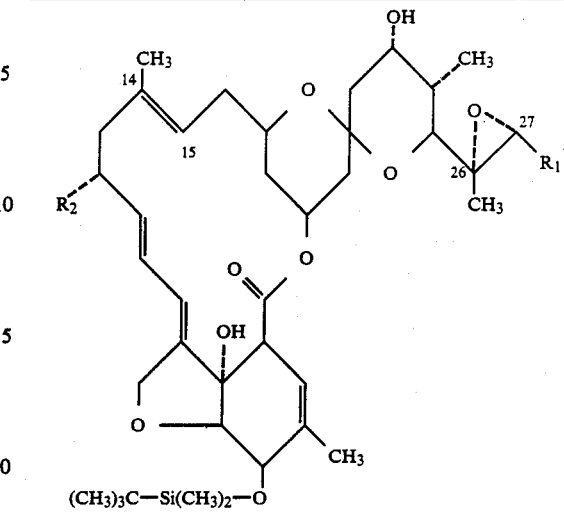

| R₁ | R₂ |
|---|---|
| CH(CH₃)₂ | H |
| CH₂CH₃ | CH₃ |
| CH(CH₃)₂ | CH₂CH₃ |
| CH₃ | CH₃ |

EXAMPLE 21

C(26,27)-Epoxy-23-Oxo-LL-F28249α

In 5 mL of dry CH₂Cl₂, 116 mg of 5-O-t-butyl-dimethylsilyl-C(26,27)-epoxy-LL-F28249α is stirred, and 540 mg of NaOAc is added, followed by 173 mg of pyridinum chlorochromate (PCC). The reaction is followed by HPLC, and an additional 250 mg of PCC is added to complete the oxidation. After 6 hours, the mixture is poured into ice-water mixture, and the CH₂Cl₂ layer is separated. The aqueous layer is further extracted with 5 mL of CH₂Cl₂, and the combined CH₂Cl₂ extracts are washed with H₂O and dried over anhydrous Na₂SO₄. The CH₂Cl₂ solution is evaporated in vacuo to afford a glassy residue, which is dissolved in Et₂O. The Et₂O solution is filtered, dried over anhydrous Na₂SO₄ and evaporated to dryness to give a glassy residue. This residue is dissolved in 2 mL of MeOH and at 0° C. treated with 30 mg of toluenesulfonic acid in 0.5 mL of MeOH. The mixture is stirred for 3 hours and poured into NaHCO₃ solution. After stirring, the mixture is extracted with EtOAc (5×4 mL) and the combined extracts are washed with saturated NaCl solution, dried over anhydrous Na₂SO₄ and evaporated to dryness. The residue is purified by chromatography over SiO₂ using 10% isopropanol/CH₂Cl₂ to afford the title compound, which is identified by mass spectrometry and NMR spectroscopy.

Substitution of PCC with pyridinium dichromate (PDC) in the above procedure also affords the title compound.

EXAMPLES 22-25

Using the procedure described in Example 21, the following C(26,27)-epoxy-23-oxo-LL-F28249 compounds are prepared:

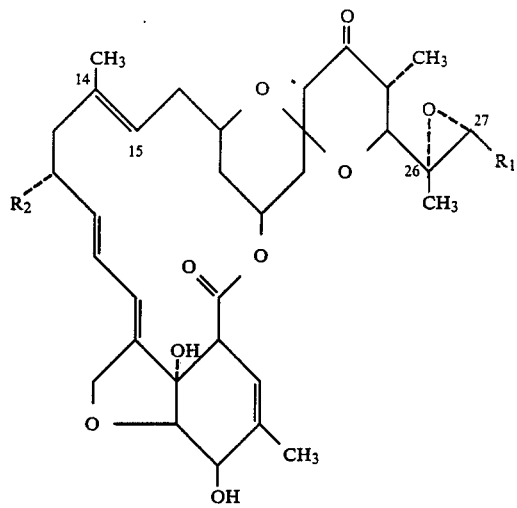

| $R_1$ | $R_2$ |
|---|---|
| CH(CH$_3$)$_2$ | H |
| CH$_2$CH$_3$ | CH$_3$ |
| CH(CH$_3$)$_2$ | CH$_2$CH$_3$ |
| CH$_3$ | CH$_3$ |

EXAMPLE 26

C(26,27)-epoxy-23-methoxime-LL-F28249α

In 1 mL of dioxane, 70 mg of C(26,27)-epoxy-23-oxo-LL-F28249α, 12 mg of NaOAc, 12 mg of CH$_3$ONH$_2$·HCl and a drop of HOAc are stirred at room temperature until the reaction is complete by HPLC monitoring (3 days). The mixture is evaporated to near dryness and diluted with 5 mL of H$_2$O. The aqueous mixture is extracted with CH$_2$Cl$_2$ (4×2 mL) and the combined extracts are washed with H$_2$O, dried over anhydrous Na$_2$SO$_4$ and evaporated to dryness. The residue is dissolved in Et$_2$O (5 mL) and washed with H$_2$O (3×2 mL), dried over anhydrous Na$_2$SO$_4$ and evaporated to dryness to afford the title compound, which is analyzed by mass spectrometry and NMR spectroscopy to confirm its structure.

EXAMPLES 27–38

Using the method of Example 26, the following C(26,27)-epoxide-23-substituted oximino-LLF28249 compounds are prepared using the appropriate R$_3$ONH$_2$·HCl:

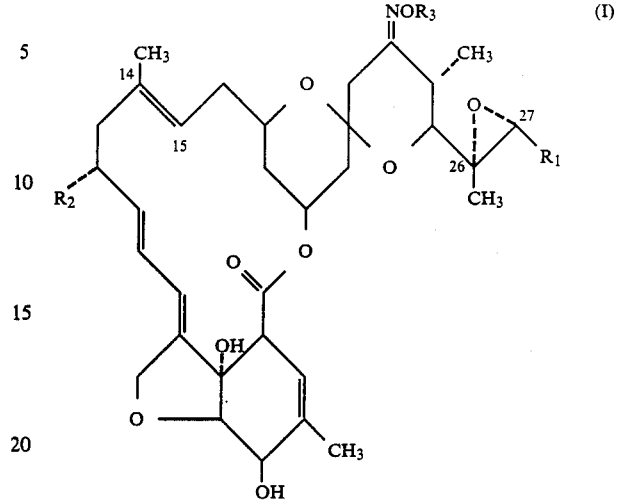

| $R_1$ | $R_2$ | $R_3$ |
|---|---|---|
| CH(CH$_3$)$_2$ | H | CH$_3$ |
| CH$_2$CH$_3$ | CH$_3$ | CH$_3$ |
| CH(CH$_3$)$_2$ | CH$_2$CH$_3$ | CH$_3$ |
| CH$_3$ | CH$_3$ | CH$_3$ |
| CH(CH$_3$)$_2$ | CH$_3$ | C$_2$H$_5$ |
| CH(CH$_3$)$_2$ | CH$_3$ | n-C$_6$H$_{13}$ |
| CH(CH$_3$)$_2$ | CH$_3$ | H |
| CH(CH$_3$)$_2$ | CH$_3$ | i-C$_3$H$_7$ |
| CH(CH$_3$)$_2$ | CH$_3$ | C$_6$H$_5$ |
| CH(CH$_3$)$_2$ | CH$_3$ | Allyl |
| CH(CH$_3$)$_2$ | CH$_3$ | Propargyl |
| CH(CH$_3$)$_2$ | CH$_3$ | C$_2$H$_5$OCOCH$_2$ |

EXAMPLE 39

C(26,27)-epoxy-23-semicarbazone-LL-F28249α

In 6 mL of dioxane, 60 mg of C(26,27)-epoxy-23-oxo-LL-F28249α is stirred with 56.4 mg of NaOAc, 77 mg of semicarbazide hydrochloride and 18 μl of HOAc for 7 days at room temperature. The mixture is poured on ice-H$_2$O mixture, and the composite is extracted with CH$_2$Cl$_2$ (3×15 mL). The combined extracts are washed with H$_2$O and evaporated to afford a glassy residue. The residue is dissolved in 50 mL of Et$_2$O and the Et$_2$O solution is washed with H$_2$O (8×20 mL), dried over anhydrous Na$_2$SO$_4$ and evaporated to afford the title compound, which is identified by mass spectrometry and NMR spectroscopy.

EXAMPLES 40–46

Using the method of Example 39, the following compounds are prepared by using the appropriate semicarbazide hydrochloride:

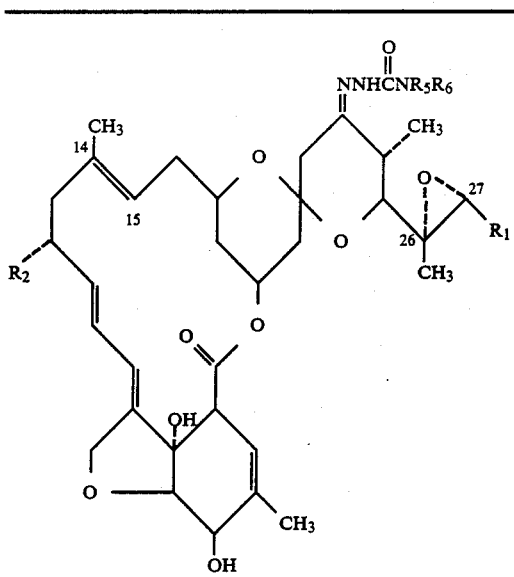

| $R_1$ | $R_2$ | $R_5$ | $R_6$ |
|---|---|---|---|
| $CH(CH_3)_2$ | H | H | H |
| $CH_2CH_3$ | $CH_3$ | H | H |
| $CH(CH_3)_2$ | $CH_2CH_3$ | H | H |
| $CH_3$ | $CH_3$ | H | H |
| $CH(CH_3)_2$ | $CH_3$ | H | $CH_3$ |
| $CH(CH_3)_2$ | $CH_3$ | $CH_3$ | $CH_3$ |
| $CH(CH_3)_2$ | $CH_3$ | H | $n\text{-}C_4H_9$ |

EXAMPLE 47

C(26,27)-epoxy-23-(2-formylhydrazone)-LL-F28249α

In 20 mL of MeOH, 50 mg of C(26,27)-epoxy-23-oxo-LL-F28249α is stirred with 25 mg of formylhydrazide in the presence of 10 μl of HOAc. The mixture is stirred for 3 days and poured on ice. The aqueous portion is saturated with NaCl. The H₂O mixture is extracted with CH₂Cl₂ (3×10 mL), and the extracts are dried over Na₂SO₄ and evaporated to dryness to afford the title compound, which is identified by mass spectrometry and NMR spectroscopy.

EXAMPLES 48–57

Using the procedure of Example 47, the following 23-(substituted hydrazones) are prepared by using the appropriate substituted hydrazine:

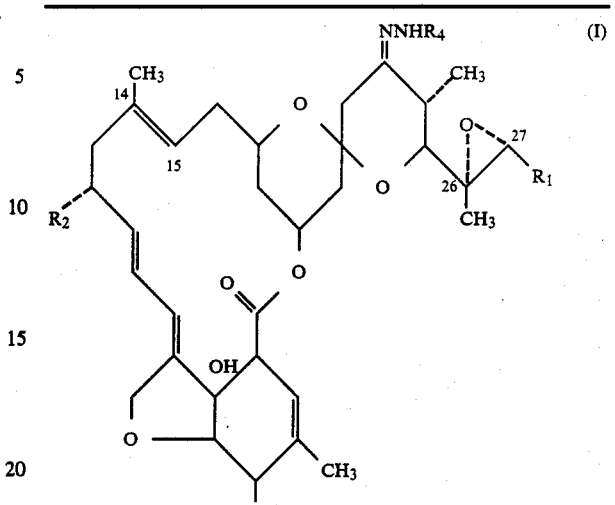

| $R_1$ | $R_2$ | $R_4$ |
|---|---|---|
| $CH(CH_3)_2$ | H | CHO |
| $CH_2CH_3$ | $CH_3$ | CHO |
| $CH(CH_3)_2$ | $CH_2CH_3$ | CHO |
| $CH_3$ | $CH_3$ | CHO |
| $CH(CH_3)_2$ | $CH_3$ | $CH_3CO$ |
| $CH(CH_3)_2$ | $CH_3$ | $C_3H_7CO$ |
| $CH(CH_3)_2$ | $CH_3$ | $CH_3OC(O)-$ |
| $CH(CH_3)_2$ | $CH_3$ | $C_2H_5OC(O)-$ |
| $CH(CH_3)_2$ | $CH_3$ | $C_4H_9OC(O)-$ |
| $CH(CH_3)_2$ | $CH_3$ | $C_2H_5CO$ |

EXAMPLE 58

C(26,27)-epoxy-23-[O-(methylcarbamoyl)oxime]-LL-F28249α

In 5 mL of Et₂O, 25 mg of C(26,27)-epoxy-23-oxime-LL-F28249α as stirred under N₂ with 10 μl of Et₃N and 50 μl of methyl isocyanate for 18 hours at room temperature. The mixture is evaporated to dryness and the residue is purified on preparative chromatography plate (SiO₂) using 10% MeOH/CH₂Cl₂ to afford the title compound which is identified by mass spectrometry and NMR spectroscopy.

EXAMPLES 59–70

Using the procedure of Example 59, the following compounds are prepared by using appropriate oximes and isocyanates.

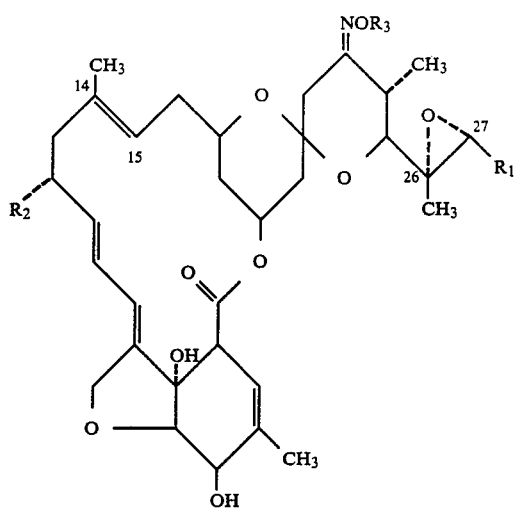

| $R_1$ | $R_2$ | $R_3$ |
|---|---|---|
| $CH(CH_3)_2$ | H | $CH_3NHCO$ |
| $CH_2CH_3$ | $CH_3$ | $CH_3NHCO$ |
| $CH(CH_3)_2$ | $CH_2H_3$ | $CH_3NHCO$ |
| $CH_3$ | $CH_3$ | $CH_3NHCO$ |
| $CH(CH_3)_2$ | $CH_3$ | $C_2H_5NHCO$ |
| $CH(CH_3)_2$ | $CH_3$ | $i\text{-}C_3H_7NHCO$ |
| $CH(CH_3)_2$ | $CH_3$ | $n\text{-}C_4H_9NHCO$ |
| $CH(CH_3)_2$ | $CH_3$ | $CH_2=CH_2CH_2NHCO$ |
| $CH(CH_3)_2$ | $CH_3$ | $HC\equiv CCH_2NHCO$ |
| $CH(CH_3)_2$ | $CH_3$ | $C_6H_5CH_2NHCO$ |
| $CH(CH_3)_2$ | $CH_3$ | $4\text{-}ClC_6H_4NHCO$ |
| $CH(CH_3)_2$ | $CH_3$ | $3,4\text{-}Cl_2C_6H_3NHCO$ |

EXAMPLE 71

C(26,27)-epoxy-23-[O-(acetyl)oxime]-LL-F28249α

In 1 mL of $CH_2Cl_2$, 64 mg of C(26,27)-epoxy-23-oxime-LL-F28249α is stirred at 0° C. with 6 μl of triethylamine and 5 mL of a solution containing 244.2 mg of $Ac_2O$ in 100 mL of $CH_2Cl_2$ is added. The mixture is stirred at 0° C. for 24 hours and evaporated to dryness to afford the title compound.

EXAMPLES 72–80

Using the procedure of Example 71, the following compounds are prepared by reacting the appropriate oximes and acid anhydrides:

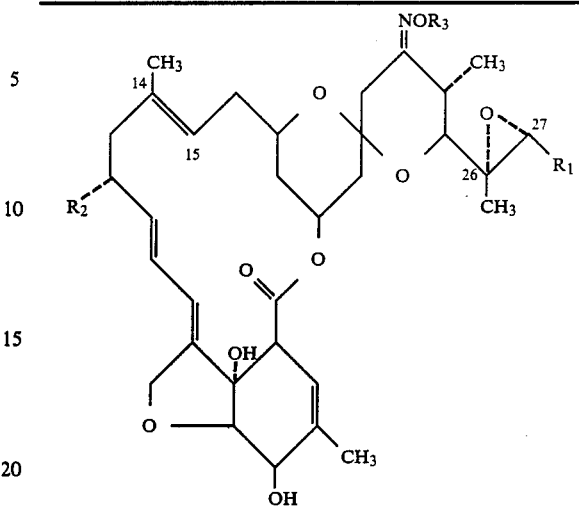

| $R_1$ | $R_2$ | $R_3$ |
|---|---|---|
| $CH(CH_3)_2$ | H | $CH_3CO$ |
| $CH_2CH_3$ | $CH_3$ | $CH_3CO$ |
| $CH(CH_3)_2$ | $CH_2CH_3$ | $CH_3CO$ |
| $CH_3$ | $CH_3$ | $CH_3CO$ |
| $CH(CH_3)_2$ | $CH_3$ | $CH_3OCH_2CO$ |
| $CH(CH_3)_2$ | $CH_3$ | $ClCH_2CO$ |
| $CH(CH_3)_2$ | $CH_3$ | $C_6H_5CH_2CO$ |
| $CH(CH_3)_2$ | $CH_3$ | $C_6H_5CO$ |
| $CH(CH_3)_2$ | $CH_3$ | 4-Chlorobenzoyl |

EXAMPLES 81–87

Using the procedure of Example 47, the following compounds are prepared by reacting the appropriate substituted hydrazines and 23-oxo compounds:

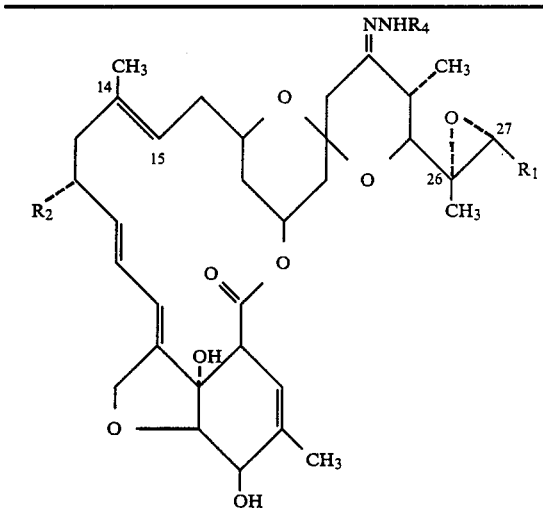

| $R_1$ | $R_2$ | $R_4$ |
|---|---|---|
| $CH(CH_3)_2$ | H | $CH_3$ |
| $CH_2CH_3$ | $CH_3$ | $CH_3$ |
| $CH(CH_3)_2$ | $CH_2CH_3$ | $CH_3$ |
| $CH_3$ | $CH_3$ | $CH_3$ |
| $CH(CH_3)_2$ | $CH_3$ | $CH_3$ |
| $CH(CH_3)_2$ | $CH_3$ | $CH_2CH_3$ |
| $CH(CH_3)_2$ | $CH_3$ | $t\text{-}C_4H_9$ |

EXAMPLE 88

5-O-t-butyldimethylsilyl-C(14,15;26,27)-diepoxy-LL-F28249α

Using the procedure of Example 16, the title compound is prepared.

EXAMPLE 89

C(14,15;26,27)-diepoxy-23-oxo-LL-F28249α

Using the method of Example 21, the title compound is prepared and identified by mass spectrometry and NMR spectroscopy.

EXAMPLES 90-95

Using the method of Example 26, the following compounds are prepared:

R_3
CH_3
C_2H_5
i-C_3H_7
n-C_6H_13
Allyl
Propargyl

EXAMPLES 96-104

Using the method of Example 47, the following compounds are prepared:

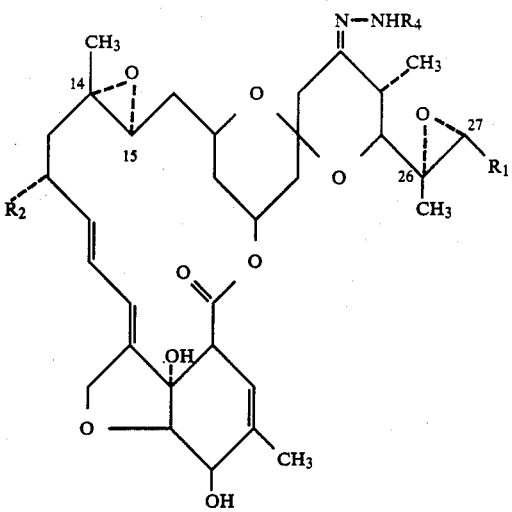

| $R_1$ | $R_2$ | $R_4$ |
|---|---|---|
| $CH(CH_3)_2$ | H | CHO |
| $CH_2CH_3$ | $CH_3$ | CHO |
| $CH(CH_3)_2$ | $CH_2CH_3$ | CHO |
| $CH_3$ | $CH_3$ | CHO |
| $CH(CH_3)_2$ | $CH_3$ | CHO |
| $CH(CH_3)_2$ | $CH_3$ | $C_3H_7CO$ |
| $CH(CH_3)_2$ | $CH_3$ | $CH_3OC(=O)-$ |
| $CH(CH_3)_2$ | $CH_3$ | $C_2H_5OC(=O)-$ |
| $CH(CH_3)_2$ | $CH_3$ | $C_2H_5C(=O)-$ |

EXAMPLES 105-111

Using the method of Example 39, the following compounds are prepared by using the appropriate semicarbazide hydrochloride:

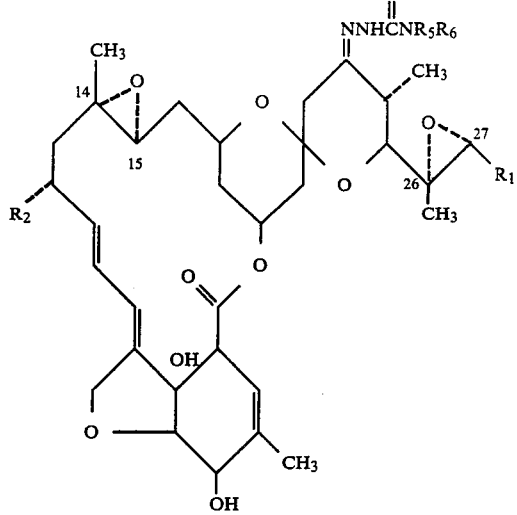

| $R_1$ | $R_2$ | $R_5$ | $R_6$ |
|---|---|---|---|
| $CH(CH_3)_2$ | H | H | H |
| $CH_2CH_3$ | $CH_3$ | H | H |
| $CH(CH_3)_2$ | $CH_2CH_3$ | H | H |
| $CH_3$ | $CH_3$ | H | H |
| $CH(CH_3)_2$ | $CH_3$ | H | $CH_3$ |
| $CH(CH_3)_2$ | $CH_3$ | $CH_3$ | $CH_3$ |
| $CH(CH_3)_2$ | $CH_3$ | H | $n\text{-}C_4H_9$ |

What is claimed is:

1. A compound represented by structural formula (I):

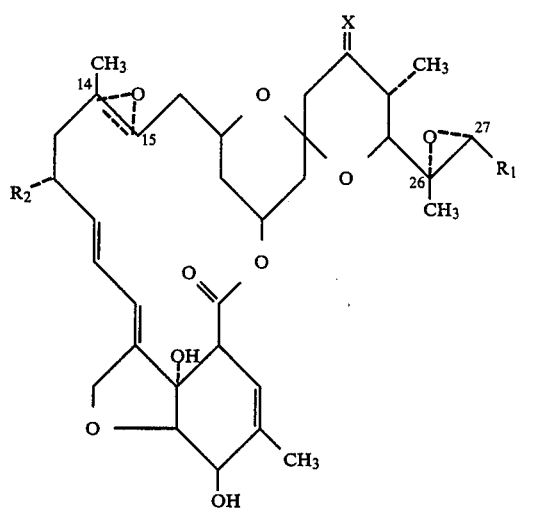

wherein $R_1$ is methyl or isopropyl; $R_2$ is hydrogen, methyl or ethyl; X is oxygen, $NOR_3$, or $N\text{—}NHR_4$; $R_3$ is hydrogen, $C_1$-$C_6$ alkyl, benzyl, allyl, propargyl, phenyl, $CH_2COO$-alkyl ($C_1$-$C_4$), $N$-($C_1$-$C_6$ alkyl)carbamoyl, $N$-(allyl)carbamoyl, $N$-(propargyl) carbamoyl, $N$-(phenyl)carbamoyl, $N$-(chlorophenyl)carbamoyl, $N$-(dichlorophenyl)carbamoyl, $N$-(benzyl)carbamoyl, $C_1$-$C_6$ alkanoyl, chloroacetyl, methoxyacetyl, phenylacetyl, benzoyl or chlorobenzoyl; $R_4$ is

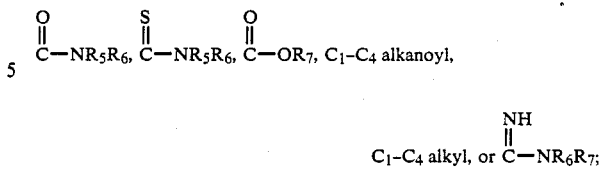

$R_5$ and $R_6$ are hydrogen or $C_1$-$C_4$ alkyl; $R_7$ is $C_1$-$C_4$ alkyl; and the dotted triangular figure with oxygen at C(14, 15) indicates that either a double bond or an epoxide is present; with the proviso that $R_2$ cannot be methyl when X is oxygen or $NOR_3$ and $R_3$ is hydrogen, $C_1$-$C_6$ alkyl or allyl.

2. The compound according to claim 1, wherein $R_1$ is isopropyl; $R_2$ is methyl; X is $NOR_3$ or $NNHR_4$; $R_3$ is as defined in claim 1 with the proviso that $R_3$ cannot be hydrogen, $C_1$-$C_6$ alkyl or allyl and $R_4$ is $$\overset{O}{\underset{}{\overset{\|}{C}}}NR_5R_6, \overset{O}{\underset{}{\overset{\|}{C}}}OR_7,$$

$C_1$-$C_4$ alkanoyl or $C_1$-$C_4$ alkyl.

3. The compound according to claim 2, wherein, $R_1$ is isopropyl; $R_2$ is methyl; X is $NOR_3$ or $NNHR_4$; $R_4$ is

or $C_1$-$C_4$ alkanoyl; and the dotted triangular figure with oxygen at C(14,15) represents a double bond.

4. The compound according to claim 1, wherein $R_1$ is isopropyl; $R_2$ is methyl; X is

and the dotted triangular figure with oxygen at C(14,15) represents a double bond.

5. The compound according to claim 1, wherein $R_1$ is isopropyl; $R_2$ is hydrogen or ethyl; X is $NOCH_3$; and the dotted triangular figure with oxygen at C(14,15) represents a double bond.

6. A method for the prevention, treatment or control of endoparasitic or ectoparasitic infections in warm-blooded animals, said method comprising: orally, topically or parenterally administering to an animal infected with endo- or ectoparasites, an endo- or extoparasiticidally effective amount of a compound represented by structural formula (I),

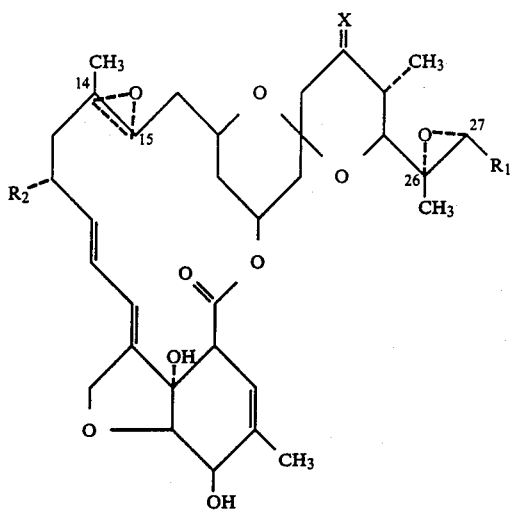

wherein $R_1$ is methyl or isopropyl; $R_2$ is hydrogen, methyl or ethyl; X is oxygen, $NOR_3$, or $N-NHR_4$; $R_3$ is hydrogen, $C_1-C_6$ alkyl, benzyl, allyl, propargyl, phenyl, $CH_2COO$-alkyl ($C_1-C_4$), N-($C_1-C_6$ alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1-C_6$ alkanoyl, chloroacetyl, methoxyacetyl, phenylacetyl, benzoyl or chlorobenzoyl; $R_4$ is

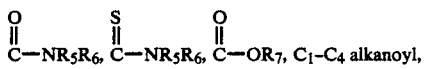

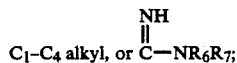

$R_5$ and $R_6$ are hydrogen or $C_1-C_4$ alkyl; $R_7$ is $C_1-C_4$ alkyl; and the dotted triangular figure with oxygen at C(14, 15) indicates that either a double bond or an epoxide is present; with the proviso that $R_2$ cannot be methyl when X is oxygen or $NOR_3$ and $R_3$ is hydrogen, $C_1-C_6$ alkyl or allyl.

7. The method according to claim 6, wherein said compound is $R_1$ as isopropyl; $R_2$ as methyl; X is $NOR_3$ or $N-NHR_4$; $R_3$ is as defined in claim 6 with the proviso that $R_3$ cannot be hydrogen, $C_1-C_6$ alkyl or allyl and $R_4$ is

$C_1-C_4$ alkanoyl or $C_1-C_4$ alkyl.

8. The method according to claim 7, wherein said compound is $R_1$ as isopropyl; $R_2$ is methyl; X is $NOR_3$ or $NNHR_4$; $R_4$ is

or $C_1-C_4$ alkanoyl; and the dotted triangular figure with oxygen at C(14, 15) represents a double bond.

9. The method according to claim 6, wherein said compound is $R_1$ as isopropyl; $R_2$ is methyl; X is

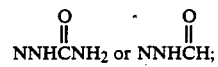

and the dotted triangular figure with oxygen at C(14, 15) represents a double bond.

10. The method according to claim 6, wherein said compound is $R_1$ as isopropyl; $R_2$ is hydrogen or ethyl; X is $NOCH_3$; and the dotted triangular figure with oxygen at C(14, 15) represents a double bond.

11. A method for controlling insects which attack crops, trees, shrubs, stored grains and ornamentals, said method comprising: applying to said crops, trees, shrubs, stored grains and ornamentals an insecticidally effective amount of a compound represented by structural formula (I),

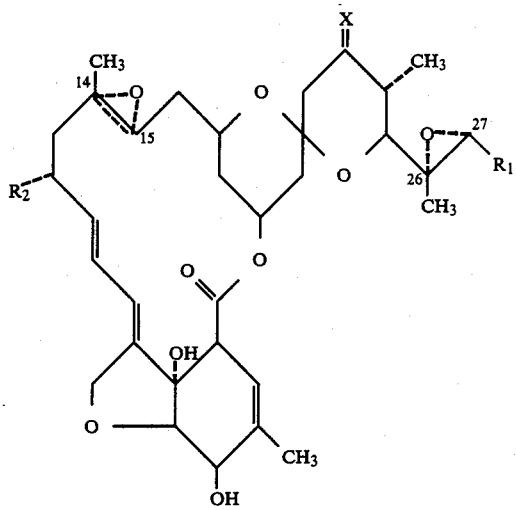

wherein $R_1$ is methyl or isopropyl; $R_2$ is hydrogen, methyl or ethyl; X is oxygen, $NOR_3$, or $N-NHR_4$; $R_3$ is hydrogen, $C_1-C_6$ alkyl, benzyl, allyl, propargyl, phenyl, $CH_2COO$-alkyl ($C_1-C_4$), N-($C_1-C_6$ alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1-C_6$ alkanoyl, chloroacetyl, methoxyacetyl, phenylacetyl, benzoyl or chlorobenzoyl; $R_4$ is

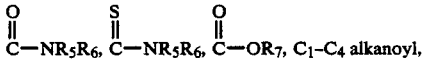

$R_5$ and $R_6$ are hydrogen or $C_1-C_4$ alkyl; $R_7$ is $C_1-C_4$ alkyl; and the dotted triangular figure with oxygen at C(14, 15) indicates that either a double bond or an epoxide is present; with the proviso that $R_2$ cannot be methyl when X is oxygen or $NOR_3$ and $R_3$ is hydrogen, $C_1-C_6$ alkyl or allyl.

12. The method according to claim 11, wherein said compound is $R_1$ as isopropyl; $R_2$ as methyl; X is $NOR_3$ or $N-NHR_4$; $R_3$ is as defined in claim 11 with the proviso that $R_3$ cannot be hydrogen, $C_1-C_6$ alkyl or allyl and $R_4$ is $$\underset{\text{CNR}_5\text{R}_6,}{\overset{\text{O}}{\|}} \underset{\text{COR}_7,}{\overset{\text{O}}{\|}}$$

$C_1$-$C_4$ alkanoyl or $C_1$-$C_4$ alkyl.

13. The method according to claim 12, wherein said compound is $R_1$ as isopropyl; $R_2$ is methyl; X is $NOR_3$ or $NNHR_4$; $R_3$ is as defined in claim 12; $R_4$ is $$\underset{\text{CNR}_5\text{R}_6}{\overset{\text{O}}{\|}}$$

or $C_1$-$C_4$ alkanoyl; and the dotted triangular figure with oxygen at C(14, 15) represents a double bond.

14. The method according to claim 11, wherein said compound is $R_1$ as isopropyl; $R_2$ is methyl; X is $$\underset{\text{NNHCNH}_2}{\overset{\text{O}}{\|}} \text{ or } \underset{\text{NNHCH;}}{\overset{\text{O}}{\|}}$$

and the dotted triangular figure with oxygen at C(14, 15) represents a double bond.

15. The method according to claim 11, wherein said compound is $R_1$ as isopropyl; $R_2$ is hydrogen or ethyl; X is $NOCH_3$; and the dotted triangular figure with oxygen at C(14, 15) represents a double bond.

16. A method for the control of plant nematodes, said method comprising: applying to the foliage of plants, the soil in which they are grown or into the trunks thereof, a nematocidally-effective amount of a compound represented by structural formula (I), wherein $R_1$ is methyl or isopropyl; $R_2$ is hydrogen, methyl or ethyl; X is oxygen, $NOR_3$, or N—$NHR_4$; $R_3$ is hydrogen, $C_1$-$C_6$ alkyl, benzyl, allyl, propargyl, phenyl, $CH_2COO$-alkyl ($C_1$-$C_4$), N-($C_1$-$C_6$ alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1$-$C_6$ alkanoyl, chloroacetyl, methoxyacetyl, phenylacetyl, benzoyl or chlorobenzoyl; $R_4$ is $$\underset{\text{C—NR}_5\text{R}_6,}{\overset{\text{O}}{\|}} \underset{\text{C—NR}_5\text{R}_6,}{\overset{\text{S}}{\|}} \underset{\text{C—OR}_7,}{\overset{\text{O}}{\|}} C_1\text{-}C_4 \text{ alkanoyl,}$$

$$C_1\text{-}C_4 \text{ alkyl, or } \underset{\text{C—NR}_6\text{R}_7;}{\overset{\text{NH}}{\|}}$$

$R_5$ and $R_6$ are hydrogen or $C_1$-$C_4$ alkyl; $R_7$ is $C_1$-$C_4$ alkyl; and the dotted triangular figure with oxygen at C(14, 15) indicates that either a double bond or an epoxide is present; with the proviso that $R_2$ cannot be methyl when X is oxygen or $NOR_3$ and $R_3$ is hydrogen, $C_1$-$C_6$ alkyl or allyl.

17. The method according to claim 16, wherein said compound is $R_1$ as isopropyl; $R_2$ as methyl; X is $NOR_3$ or N—$NHR_4$; $R_3$ is as defined in claim 16 with the proviso that $R_3$ cannot be hydrogen, $C_1$-$C_6$ alkyl or allyl and $R_4$ is $$\underset{\text{CNR}_5\text{R}_6,}{\overset{\text{O}}{\|}} \underset{\text{COR}_7,}{\overset{\text{O}}{\|}}$$

$C_1$-$C_4$ alkanoyl or $C_1$-$C_4$ alkyl.

18. The method according to claim 17, wherein said compound is $R_1$ as isopropyl; $R_2$ is methyl; X is $NOR_3$ or $NNHR_4$; $R_3$ is as defined in claim 17; $R_4$ is $$\underset{\text{CNR}_5\text{R}_6}{\overset{\text{O}}{\|}}$$

or $C_1$-$C_4$ alkanoyl; and the dotted triangular figure with oxygen at C(14, 15) represents a double bond.

19. The method according to claim 16, wherein said compound is $R_1$ as isopropyl; $R_2$ is methyl; X is $$\underset{\text{NNHCNH}_2}{\overset{\text{O}}{\|}} \text{ or } \underset{\text{NNHCH;}}{\overset{\text{O}}{\|}}$$

and the dotted triangular figure with oxygen at C(14, 15) represents a double bond.

20. The method according to claim 16, wherein said compound is $R_1$ as isopropyl; $R_2$ is hydrogen or ethyl; X is $NOCH_3$; and the dotted triangular figure with oxygen at C(14, 15) represents a double bond.

21. A composition comprising a pharmacologically-effective amount of a compound represented by structural formula (I),

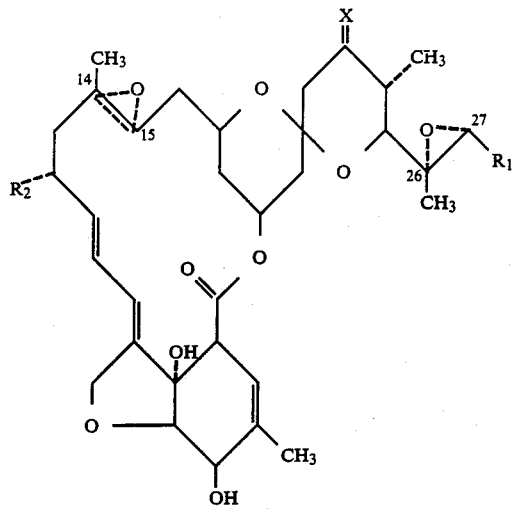 (I)

wherein $R_1$ is methyl or isopropyl; $R_2$ is hydrogen, methyl or ethyl; X is oxygen, $NOR_3$, or $N-NHR_4$; $R_3$ is hydrogen, $C_1-C_6$ alkyl, benzyl, allyl, propargyl, phenyl, $CH_2COO$-alkyl ($C_1-C_4$), N-($C_1-C_6$ alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1-C_6$ alkanoyl, chloroacetyl, methoxyacetyl, phenylacetyl, benzoyl or chlorobenzoyl; $R_4$ is

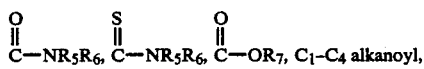

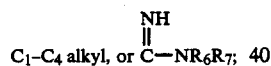

$R_5$ and $R_6$ are hydrogen or $C_1-C_4$ alkyl; $R_7$ is $C_1-C_4$ alkyl; and the dotted triangular figure with oxygen at C(14, 15) indicates that either a double bond or an epoxide is present; with the proviso that $R_2$ cannot be methyl when X is oxygen or $NOR_3$ and $R_3$ is hydrogen, $C_1-C_6$ alkyl or allyl and an inert carrier; wherein said composition is used for the control of endo- or ectoparasites which infest warm-blooded animals.

22. A composition comprising: an insecticidally-effective amount of a compound represented by the structural formula (I),

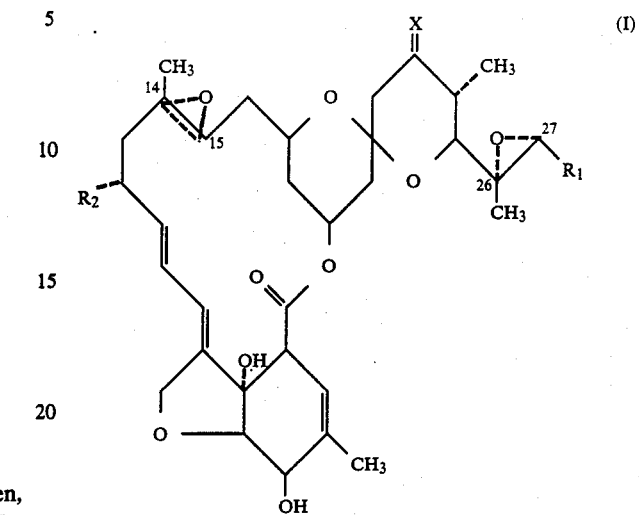 (I)

wherein $R_1$ is methyl or isopropyl; $R_2$ is hydrogen, methyl or ethyl; X is oxygen, $NOR_3$, or $N-NHR_4$; $R_3$ is hydrogen, $C_1-C_6$ alkyl, benzyl, allyl, propargyl, phenyl, $CH_2COO$-alkyl ($C_1-C_4$), N-($C_1-C_6$ alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1-C_6$ alkanoyl, chloroacetyl, methoxyacetyl, phenylacetyl, benzoyl or chlorobenzoyl; $R_4$ is

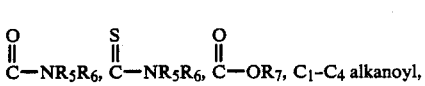

$R_5$ and $R_6$ are hydrogen or $C_1-C_4$ alkyl; $R_7$ is $C_1-C_4$ alkyl; and the dotted triangular figure with oxygen at C(14, 15) indicates that either a double bond or an epoxide is present; with the proviso that $R_2$ cannot be methyl when X is oxygen or $NOR_3$ and $R_3$ is hydrogen, $C_1-C_6$ alkyl or allyl and an inert carrier; wherein said composition controls insects or acarid pest which infest growing crops, trees, shrubs, stored grains or ornamentals.

* * * * *